United States Patent [19]
Blott et al.

[11] Patent Number: 5,514,080
[45] Date of Patent: May 7, 1996

[54] ORTHOPAEDIC CAST AND COMPONENTS THEREFORE

[75] Inventors: Patrick L. Blott, Bishops Stortford; Julian A. Webb, Harlow, both of United Kingdom

[73] Assignee: Smith & Nephew PLC, United Kingdom

[21] Appl. No.: 176,315

[22] Filed: Jan. 3, 1994

Related U.S. Application Data

[63] Continuation of Ser. No. 63,634, May 18, 1993, abandoned, which is a continuation of Ser. No. 689,069, Jun. 17, 1991, abandoned.

[30] Foreign Application Priority Data

| May 18, 1989 | [GB] | United Kingdom | 8911476 |
| May 17, 1990 | [GB] | United Kingdom | 9011076 |

[51] Int. Cl.⁶ ........................... A61F 5/00
[52] U.S. Cl. ........................... 602/5; 602/8
[58] Field of Search ............ 602/5, 6, 7, 8, 602/12, 13, 20, 21, 23, 60, 61; 128/882

[56] References Cited

U.S. PATENT DOCUMENTS

| 2,905,174 | 9/1959 | Smith | 602/42 |
| 2,960,984 | 11/1960 | Parker | 602/8 |
| 2,969,791 | 1/1961 | Ekenstam | 602/8 |
| 3,040,740 | 6/1962 | Parker | 602/8 |
| 3,307,537 | 3/1967 | Simon | 602/8 |
| 3,630,194 | 12/1971 | Boardman | 602/8 |
| 3,656,475 | 4/1972 | Hanraham | 602/8 |
| 3,935,355 | 1/1976 | Kuhn | 602/6 |
| 3,972,323 | 8/1976 | Boricheski | |
| 4,019,506 | 4/1977 | Eschmann | 602/8 |
| 4,628,917 | 12/1986 | Campagna | 602/8 |
| 4,655,208 | 4/1987 | Yoon | 602/8 |
| 4,672,956 | 6/1987 | Potter | 602/8 |
| 4,793,330 | 12/1988 | Honeycutt | 602/8 |
| 4,841,958 | 6/1989 | Ersfeld | 602/8 |
| 4,945,903 | 8/1990 | Alper | 602/5 |
| 4,989,593 | 2/1991 | Campagna | 602/8 |

FOREIGN PATENT DOCUMENTS

| 0029727 | 11/1980 | European Pat. Off. . |
| 0223366 | 9/1986 | European Pat. Off. . |
| 0249312 | 4/1987 | European Pat. Off. . |
| 0346697 | 6/1989 | European Pat. Off. . |

Primary Examiner—Michael A. Brown
Attorney, Agent, or Firm—Graham & James

[57] ABSTRACT

A casting system for application to a body portion, having an outer layer tubular substrate carrying a water hardenable resin wherein the substrate is at least 2mm thick and an inner layer having an undercast padding material that includes hydrophobic fibers or yarns.

30 Claims, 1 Drawing Sheet

ORTHOPAEDIC CAST AND COMPONENTS THEREFORE

This application is a continuation of Ser. No. 08/063,634 filed Jun. 18, 1993 now abandoned, which is a continuation of Ser. No. 07/689,069 filed Jun. 17, 1991, now abandoned.

The invention relates to casting systems, to the components of casting systems, to processes for their preparation, to methods of use and to orthopaedic casts formed therefrom.

Casting bandages are normally used in the treatment of bone fractures or deformities to form a rigid or stiff immobilising or support orthopaedic cast on a body portion, such as a foot, leg, hand or arm. The use of a thin woven substrate, typically containing yarns of cellulosic, polyester, polyolefine or glass fibres or mixtures thereof, in the form of a strip or tube to which a hardenable resin is subsequently applied after the substrate has been applied to the body portion has been proposed. These bandage substrates are applied to a body portion for example by winding a strip or sliding a tubular substrate of the substrate over the affected portion and applying the resin which upon hardening forms a cast or by winding a strip of resin impregnated substrate around the body portion and allowing the resin to harden. However, in order to provide a cast of adequate strength, it has been found necessary in the past to apply several for example four to eight layers of the resin impregnated substrate bandage to form a laminate of the superimposed substrate layers on the body portion. The present invention seeks to provide a casting system which avoids the need to apply several layers thereof to form a cast of adequate strength on a body portion.

Accordingly, the present invention provides a casting system for application to a body portion comprising a tubular substrate carrying a hardenable resin.

The tubular substrate employed in the present invention is formed integrally as a tube. Thus the substrate, carrying the hardenable resin is applied to the body portion as a formed tube.

The tubular substrate preferably will generally comprise a single layer. The single layer will be bulky and hence much thicker than the substrates used for conventional casting bandages.

The bulky substrate will generally be at least 2 mm thick (ie. at least 2 mm between the inner and outer surfaces of the tube). The substrate however, will normally be less than 10 mm thick and aptly less than 8 mm thick. The substrate will aptly be at least 3 mm thick and more aptly at least 4 mm thick. The substrate will aptly be less than 8 mm thick and more aptly be less than 6 mm thick. The substrate can favourably be 3 to 8 mm thick and can preferably be 4 to 6 mm thick, for example about 5 mm thick.

The system of the invention is normally extensible in at least the width direction and possibly also in the length direction thereof.

The casting system can suitably have an extension of at least 25%, more suitably at least 50%, favourably at least 75% and can preferably have an extension of at least 100% in the width direction, The extension of the tubular bandage can be measured by a conventional bandage extension test in which the tubular bandage in lay flat form is extended widthwise to its maximum extent, In this test the original (Ow) and stretched width (Sw) are recorded, The extension of the bandage can then be expressed as a percentage of the original width using the formula extension $$\% = \frac{Sw - Ow}{Ow} \times 100.$$

The extensible nature of the system allows it to be applied to and to conform to a body portion such as a limb. Extensibility may be required in the lengthwise direction where the system is intended for use in bandaging regions such as the elbow, knee or ankle and heel.

Desirably the casting system is elastically extensible in at least the width direction. Suitably the system will be sufficiently elastic to recover to at least 60% of its original dimensions preferably at least 80% when extended to 100% in the width direction.

Bulky and elastically extensible systems may advantageously employ tubular knitted or woven materials as the substrate of which tubular knitted substrates are preferred.

In a favoured embodiment of the invention there is provided an elastically extensible casting system for application to a body portion comprising a single layer of knitted substrate carrying a body-portion immobilising amount of a hardenable resin.

Suitable methods for producing tubular knitted substrates include those used for making thick socks or stockinette. Such methods include both weft and warp knitting methods and include knitting patterns such as pillar knitting, rib or cable knitting, knitting with crimped yarns or looped yarns for example "Terry" towelling and combinations of these knitting methods. The tubular knitted substrate however may advantageously contain holes or apertures in addition to the normal yarn interstices.

The yarns employed for the knitting process can comprise the so called 'high tenacity yarns' which although they can be readily knitted, have a resistance to deformation and thus an 'apparent resilience'. The tubular knitted substrate can comprise yarns of hydrophilic or hydrophobic fibres or a combination of these fibres. Suitable hydrophilic fibres include cellulosic fibres such as cotton, viscose or acetate rayon fibres. Suitable hydrophobic fibres include acrylic, polyester and polyolefine fibres such as high density polyethylene or polypropylene fibres. Other fibres such as polyamide fibres, however, may also be present in the bandage. Glass or carbon fibre may also be knitted up, for example by weft knitting to produce a suitable substrate.

Yarns suitable for use in the invention include polypropylene 420 dernier/70 filament yarns such as those manufactured be Plasticizer Ltd, E-Glass fibres (50 Tex, 6μm filament) yarn sold by Pittsburgh Plate Glass Company and 110tex/200 filament Polyester yarn sold by Hoechst UK Ltd under the designation 'Type 730'.

Favoured tubular knitted substrates of the invention comprise yarns of hydrophobic fibres to render the substrate non-absorbent to water and aqueous fluids.

The tubular substrate used in the invention preferably also comprises an elastic component such as elastic yarn to render the tube elastically extensible in the width direction. The elastic extension of the substrate should be sufficient to permit elastic extension of the resin laden system within the aforementioned ranges.

The elastic yarn can be a mono or multifilament yarn of an elastomer such as rubber polyurethane for example Lycra or Spandex yarn or an A - B - A block copolymer for example styrshe - butadiene - styrshe copolymer sold under the Trade Mark CARIFLEX and styrene-ethylene-butylene-styrene polymers sold under the Trade Mark KRATON. The elastic component of such elastic yarns may be surrounded by sheath of a suitable material such as a polyamide, eg. Nylon. Suitable sheathed rubber based elastic yarns include yarns sold by Heathcotes Ltd under the trade designations 'Fifties' or 'Seventy fives' which are polyamide sheathed yrns containing respectively 50 and 75 rubber filaments per linear inch (2.54 cm). The elastic yarn can be attached to or included in the tubular knitted substrate as a component which extends in circular or spiral manner around the circumference of the tube. Preferably the elastic yarn is included into the tube during the knitting process. Such knitting processes can be those conventionally used for making elastic tubular bandages or elastic stockings. Rubber filaments may be included, with advantage into glass fibre knitted substrates.

Other materials suitable for the tubular substrate include woven and non-woven materials such as lofted non-woven fabrics (having fibres randomly orientated in all three dimensions) and foam materials.

Substrates comprising hydrophilic fibres may also be pretreated with a water-proofing agent to inhibit the substrate absorbing moisture.

A tubular substrate for use in the invention which is to be used on the hand, wrist or lower arm may advantageously be coloured, for example patterned. Similarly, a tubular substrate for a bandage which is to be used on the foot, ankle or lower leg may advantageously be coloured, for example patterned. One or more differently coloured materials such as yarns may be employed for the substrate for example a knitted substrate may be produced where different coloured yarns are employed to produce a pattern such as a tartan. Such coloured or patterned substrates in combination with a substantially transparent and colourless hardenable resin can provide a bandage cast which is not as conspicuous as a normal plaster cast and may render the cast more aesthestically acceptable.

The casting system of the invention further comprises a hardenable resin. The resin can be any suitable hardenable resin for orthopaedic cast bandages. Suitable hardenable resins include water hardenable or actinic radiation (visible or UV) activated hardenable resins. Favoured hardenable resins are water hardenable resins including polyurethane or acrylic prepolymer hardenable resins.

Suitable prepolymer resins of this type can be selected from those conventionally used for orthopaedic casts. Preferred hardenable resins, however, are polyurethane prepolymer resins. Such resins are typically reaction products of a polyisocyanate and a polyol such as a polyether diol optionally containing a triol. These resins may contain a catalyst such as a tertiary amine and/or a stabiliser such as an acidic material. Preferred catalysts are dimorpholino diethylether and bis(2,6—dimorpholino) diethylether. Preferred stabilisers are methane sulphonic acid and succinic anhydride.

Suitable water hardenable polyurethane propolymer resins containing catalysts and/or stabilisers of this type are disclosed in International Patent Application No. 86/01397, U.S. Pat. No. 4,433,680 and United Kingdom Patent No. 2196944 the disclosure of which is incorporated herein by reference. Other resins suitable for use in the present invention include those described in International Publication No. WO89/08463 and in British Patent Specification No. 2207141.

The hardenable resin will normally be in a liquid state to facilitate the impregnation or coating process. Hardenable propolymer resins for example polyurethane or acrylic prepolymer resins are preferably liquid at temperatures between 10° to 30° C. Solid or highly viscous prepolymers can be rendered liquid by any suitable method such as a hot melt or solvent method. The tubular substrate can be coated or impregnated with liquid prepolymer by conventional methods such as a two roll nip coating or impregnating method.

When the liquid prepolymer resin is a water hardenable resin it is desirable to dry the substrate for example by oven or vacuum drying prior to coating or impregnation to reduce the water content thereof to less than 1% by weight and preferably to less than 0.1% by weight.

The bulky substrate of the system of the invention can carry a relatively large amount of resin when compared to the amount carried by a single layer of conventional substrate. The weight of hardenable resin per unit area of the substrate will aptly be in excess of 50 g/m$^2$.

The weight per unit area of the hardenable resin on the tubular bulky substrate should normally be sufficient to immobilise the body portion encased in the system when the resin has hardened. This is known as the "body portion immobilising amount". Aptly, this amount will be at least 100 g/m$^2$ suitably from 100 to 600 g/m$^2$ and often from 300 to 500 g/m$^2$ when the application is not load bearing. For load bearing applications such as leg casts the resin weight may be greater than 1000 g/m$^2$ for example from 2000 to 9000 g/m$^2$.

The system may be provided with apertures or holes in addition to those provided by the interstices in the fabric forming the substrates to allow the hardened cast to be breathable. The holes need to be sufficiently large such that they do not fill up with resin when the substrate is impregnated or coated with the resins.

Aptly the area of each hole or aperture can be from 1 to 100 mm$^2$. Suitably the area of each tube will be not more than 15 mm$^2$, more suitably about 10 mm$^2$. The density of the holes or apertures will depend upon such factors as the required strength of the cast and the breathability required. Aptly the distribution will not be greater than about one per 50 cm$^2$.

The holes or apertures maybe mechanically formed in the substrate prior to coating or impregnation of the resin. However, where knitted substrates are employed holes of a suitable size and distribution can be included within the knitting pattern of the knitted substrate.

The combination of the relatively large amount of resin used and relatively large thickness of the bulky substrate ensures that the cast, although it comprises only a single layer of substrate, is sufficiently strong to support or immobilise a body portion to which it is applied. The walls of the orthopaedic cast will preferably be porous to allow the transmission of moisture vapour. The walls of the case may be provided with additional apertures or holes as hereinbefore mentioned to render the cast highly permeable to moisture vapour.

In yet a further aspect the present invention provides a process for the preparation of a system of the invention which comprises coating or impregnating a tubular substrate with a hardenable resin. Aptly the substrate will be a single layer. Preferably the substrate will be a bulky knitted substrate.

In accordance with a further embodiment of the invention there is provided a tubular substrate for use in a casting system.

The substrate is adapted to carry a hardenable resin and is aptly in the form of a single layer. Preferably the substrate is in the form of a tubular knitted substrate.

The tubular substrates carrying the hardenable resins is preferably used in combination with an undercast padding.

Thus the casting system of the invention may include an outer layer comprising a tubular substrate carrying a hardenable resin and an inner layer comprising an undercast padding material.

A padding material such as the tubular padding material disclosed in European Patent Application No. 0356078 may be applied to the body portion prior to formation of the cast thereon (to render the cast comfortable on the body).

Alternatively the resin substrate and undercast padding may be formed as a composite.

According to a further embodiment of the present invention there is provided an orthopaedic casting system for application to a body portion comprising an elastically extensible composite tubular material having an outer layer of fabric carrying a hardenable resin and an inner layer of padding material.

Preferably the inner layer is a tubular layer.

The composite tubular material of the invention can be rendered elastically extensible by means of an elastic component such as an elastic thread or yarn within one or both of the inner or outer layers or between such layers of the tubular material.

The composite can suitably have an extension of at least 25%, more suitably at least 50%, favourably at least 75% and can preferably have an extension of at least 100% in the width direction.

The extensible nature of the composite allows it to be applied to and to conform to a body portion such as a limb.

Suitable padding materials for the inner layer of the composite include extensible tubular materials made of stockinette, flexible polymeric foam or lofted non-woven fabric and combination of such materials of preferred padding material in an elastic stockinette having a lofted non-woven fabric bonded to the non-body contacting surface.

Suitable stockinette padding materials can be selected from the tubular extensible knitted or woven stockinette conventionally used as padding materials for orthopaedic bandages. Such stockinette padding materials can comprise hydrophilic or hydrophobic. fibres or mixture of such fibres. Hydrophlilic fibres such as cellulosic fibre for example cotton or viscose fibres can render the padding material moisture absorbent. Hydrophobic fibres however, can render the padding material relatively poorly water absorbent.

Favoured stockinette padding materials are tubular bulky stockinettes such as rib knitted or sliver knitted stockinettes or stockinettes containing crimped or looped yarns.

Preferably the tubular stockinette has an elastic component around its circumference such as an elastic yarn or thread to render the stockinette elastically extensible in the radial direction thereof.

Such a thread or yarn can form part of the stockinette that is a woven or knitted course or be attached to a surface of the stockinette. Favoured tubular stockinettes for use as a padding layer in the invention are those of the type conventionally used for elasticated tubular bandages such a those specified in the British Pharmacopia (1988).

Such elasticated tubular stockinette comprise a knitted fabric of ribbed structure containing a covered natural or synthetic rubber elastic thread or yarn. arranged in a spiral fashion in the tube. Typical elastic yarns or threads are covered by crimped fibres and yarns spun from cotton or a blend of cotton and viscose fibres.

Preferred padding materials for the inner layer of the composite comprise a lofted non-woven fabric.

A lofted non-woven fabric as used herein is a non-woven fabric having fibres lying in the direction of all three dimensions and of sufficient thickness to provide a cushion for an immobilising rigid cast formed on a portion of the body.

The lofted non-woven fabric used in the composite can be a wadding of natural or synthetic fibres of the type conventionally used for orthopaedic cast underpaddings.

Such a wadding can comprise hydrophilic or hydrophobic fibres or blends thereof.

Suitable hydrophilic fibres include cellulosic fibres such as cotton and viscose rayon fibres. Hydrophilic fibres can advantageously provide the lofted non-woven fabric with softness to skin and the capacity to absorb perspiration.

Suitable hydrophobic fibres include polyester, polypropylene and high density polyethylene fibres. Hydrophobic fibres can render the lofted non-woven fabric relatively non-absorbent so that any water penetrating the fabric can drain away.

The lofted non-woven fabric can also comprise meltable powder or fibres such as segmented, conjugate or bicomponent fibres of higher and lower melting points to bond the fibres in the fabric.

The lofted non-woven fabric use in the composite can suitably have a thickness of 2 to 10 mm and preferably have a thickness of 3 to 8 mm. Similarly the lofted non-woven fabric can suitably have a weight per unit area of 5 to 200 $g/m^2$.

The lofted non-woven fabric will preferably be formed in a manner to render the fabric resilient.

An apt resilient lofted non-woven fabric for use in the invention which comprises hyrophilic fibres is known as SOFFBAN natural orthopaedic padding available from Smith & Nephew. Such a non-woven fabric comprises viscose rayon fibres, has a thickness of 3.6 to 4.2 mm and a weight per unit area of 105 to 140 $g/m^2$.

An apt resilient lofted non-woven fabric which comprises hydrophobic fibres is known as SOFFBAN synthetic orthopaedic padding available from Smith & Nephew. Such a non-woven fabric comprises a blend of polyester fibres (85%) and meltable conjugate fibres (15%) having a polypropylene core surrounded by a high-density polyethylene layer, has athickness of 4.25 to 5.25 mm and a weight per unit area 7.5 to 10 $g/m^2$.

The lofted non-woven fabric used as an under padding layer in the composite will be in the form of a tube. Such a tube can comprise a spiral strip of lofted non-woven fabric or one or more strips arranged in a parallel and circumferencial manner to form a tube of fabric. The longitudinal edges of the or each strip may be stitched or otherwise adhered to each other.

The lofted non-woven fabric of the padding layer however, is advantageously both water vapour permeable to allow the escape of moisture from under the cast and water impervious to inhibit exterior water penetrating through the padding to the surface of the skin.

The non-woven fabric may be rendered both water vapour permeable and water impervious by treatment with a waterproofing agent or by a water vapour permeable, water impervious layer on a surface thereof.

Suitable waterproofing agents include non-toxic waterproofing agents used for textiles such as wax, silicone resin or fluorinated polymer waterproofing agent. Such an agent are normally available as a solution or dispersion.

Apt waterproofing agents for polyester fibre non-woven fabrics are a wax waterproofing agents in emulsion form known as Nickwax TX10 available from Nickwax Ltd. and Super pel available from Grangers Ltd.

The non-woven fabric may be treated for example by impregnation to provide the waterproof agent throughout the thickness of the fabric. Alternatively the non-woven fabric may be treated, for example by coating, to provide the waterproof agent at a surface layer of the fabric.

Suitable water vapour permeable, water impervious layers for the non-woven fabric can comprise a water insoluble polymer which is preferably also an elastomer to render the layer elastic and conformable.

Such layers can be continuous, voided or microporous.

Favoured elastomeric moisture vapour permeable layers include those formed from polyether polyurethane, polyester polyurethane, hydrophilic polyurethane and polyether-polyamide and polyester-polyether copolymers.

Suitable polyether polyurethanes are described in U.S. Pat. No. 2899411. Suitable polyester polyurethanes are described in U.S. Pat. No. 2871218. Apt polyester and polyether polurethanes are known as Estane (Trade Mark) available from B. F. Goodrich and in particular grades 5701, 5702, 5703, 5714F and 580201.

An apt polyester-polyether copolymer is known as Hytrel 4056 available from Dupont.

An apt polyether-polyamide copolymer is known as Peebax 2533 available from AtO Chemicals.

Suitable hydrophilic polyurethane layers for use in the inventions are disclosed in European Patent No. 91800.

The weight per unit area of the layers used on the non-woven fabrics can suitably be 5 to 80 g/m$^2$, more suitably 5 to 50 g/m$^2$ and can preferably be 7 to 30 g/m$^2$ for example 10 g/m$^2$.

Moisture vapour permeable lofted non-woven fabrics used in the invention can suitably have a moisture vapour transmission rate of at least 1000 g/m$^2$/24h, more suitably at least 2000 g/m$^2$/24h and preferably at least 5000 g/m$^2$/24h at 37° C. at 100% to 10% relative humidity difference. The moisture vapour transmission rate of a non-woven fabric can be readily determined by the Payne Cup Method (in the upright position) described in European Patent No. 46071.

The lofted non-woven fabric may also comprise an elastically extensible material to render conformable to the body portion. Tubes formed from or comprising such a lofted non-woven fabric therefore can comprise an elastic component or components to provide this extensibility. Preferably elastic component or components are located around the circumference of the tube to render it elastically radially extensible or expandable in the radial direction thereof.

Suitable elastic components include elastic yarns, threads or strips conventionally used in elastic fabrics made of a natural or synthetic rubber for example polyurethane.

The elastic component or components in an elastic tube of the composite can conveniently extend in a circular or spiral fashion around the circumference of the tube.

The elastic component or components can be attached to or within lofted the non-woven fabric.

In preferred embodiments of the invention the tubular lofted non-woven fabric is attached to an inner support layer of extensible material.

The inner support layer can favourably a tubular fabric such as an elastically knitted or woven stockinette or a woven or non-woven fabric tube which has been rendered elastically extensible.

The elastic component employed to render the support layer elastically extensible may be incorporated into the support layer or attached to the outside of the so that it is located between the lofted non-woven fabric and support layers.

In favoured embodiments of the invention the inner support layer has as an elastic component, an elastic thread or yarn which forms part of a woven or knitted tubular fabric or is attached to the outside of these tubular fabrics or a tubular non-woven fabric.

The non-woven fabric used for the support layer may be a "two dimensional" non-woven fabric of the type used for cover layers on absorbent pads such as sanitary towels and diapers. Such non-woven fabrics advantageously have a soft feel to the skin. Tubes of these non-woven fabrics can be formed from a strip or sheet thereof in same manner as tube of lofted non-woven fabric as hereinbefore mentioned.

In the composite the non-elastic material or materials in the wall of the tube can be compressed into folds forming circumferential corrugations running parallel to the main-axis of the tube thereby rendering the tube extensible or expandible in at least the radial direction. The wall of the tube will therefore usually exhibit substantially axial crepe, or crinkled or undulated fold pattern. Although the height of these folds will reduce as the tube is expanded example when it is being fitted over a body portion, the folds will reform and increase the thickness of the padding layer, and hence the cushioning effect of the layer when the tube is relaxed to conform with the body portion.

The lofted non-woven fabric layer can suitably be attached to the inner support layer by any conventionally heat or adhesive bonding or by a mechanical method such as stitching. These layers of the padding tube are preferably attached by a layer of moisture vapour permeable adhesive. A continuous layer of such an adhesive will advantageously also be water impervious. The adhesive can be a pressure sensitive adhesive or a heat melt adhesive.

Favoured moisture vapour permeable pressure sensitive adhesives for this purpose are the polyvinyl ether and acrylate ester adhesive disclosed in United Kingdom Patent Nos. 128063 and 2070631. An apt adhesive is a pressure sensitive adhesive copolymer of 47 parts by weight of n-butyl acrylate, 47 parts by weight of 2—ethyl hexyl acrylate and 6 parts by weight of acrylic acid made according to method disclosed in United Kingdom Patent No. 2070631.

Alternatively the layers can be heat bonded by means of a hot melt adhesive or interposed heat meltably layer.

In those applications where the resin is cured by the action of water a favoured embodiment comprises a water soluble but resin impervious barrier layer intermediate the padding and resin bearing layers. The intermediate layer may be retained by any of the methods hereinbefore described. During storage of the bandage the barrier layer prevents resin from contaminating the padding layer. However, upon immersion in water, the barrier layer is dissolved and water is permitted to enter the resin laden substrate from both sides. Preferably the inner layer is made of a hydrophobic material such that upon removal from the water bath, the padding material will rapidly dry out.

The casting system of the invention can be adapted in size to the size of the body portion to be immobilised by the cast formed by the composite. The elastically extensible nature of composite tubular material can be adapted to allow the bandage to be applied over a body extremity to the body portion and to conform therewith.

The composite construction of the inner and outer layers can be formed by bonding together or overlaying the padding and optionally any support layers forming the inner layer and the resin bearing substrate forming the outer layer. Bonding may be achieved by adhering the component layers using an adhesive ad hereinbefore described or by stitching them together.

In alternative embodiment the resin may be employed to form the bond. In one form of this embodiement the inner padding layer of the composite tubular material can advantageously have length which is greater than that of outer resin fabric layer to enable one or both end portions of the padding layer to be folded back over the end or ends of the outer fabric layer to provide a soft cuff or cuffs thereat. Such end portions can have aptly have length of 1 cm to 5 cm to provide cuffs of similar width.

In another form of this embodiment the tubular material can comprise two or more outer layers of fabric carrying a hardenable resin. When the composite tubular material comprises two or more of outer resin fabric layers the outer one of such layer can conveniently overlap the cuff formed in the padding layer to hold the cuff in place when the cast is formed.

The system of the invention can be adapted in size and shape to fit around a body portion. Where the affected body portion is an ankle or a foot the system may be in the shape of a sock optionally with its toe end removed. When the affected body portion is a wrist or hand the system may have a hole in a side portion thereof to accommodate a thumb region of the hand. The system may be an individual tube or part of a connected series of tubes, for example in the form of a continuous length of a tube from which individual tubes may be cut.

The system may be packaged within a pouch for example, where the resin is water activated a foil pack may be employed and which is impermeable to both liquid water and water vapour to inhibit premature hardening of the resin of the bandage. For light activated resins, the system may be packaged in an opaque pouch.

The system may be packaged as a flattened tube, and may have a suitable interliner to prevent adjacent portions of the innner surface of the tube from contacting each other. In an alternative arrangement the tube may be rolled up to form a "doughnut", preferably with an interliner separating adjacent surfaces of the rolled tube. Suitable interliners may be formed from wax-coated or siliconised papers and the like.

In order to assist application of the tubular system or unrolling of a prepackaged tubular system, slip agents may be incorporated into the resin or applied to the surface of the resin coated substrate. Suitable slip agents include silicones, surfactants and the like.

The system may be sterile within a bacteria-proof pack. The system be rendered sterile within the pack by a conventional sterilisation method such as gamma irradiation.

The casting system of the invention can be applied to a body portion to form a cast thereon. Thus in another aspect the invention provides a method of forming a cast on a body portion by applying thereto a casting system of the invention.

The extensible nature of the substrate or composite allows the system to be applied to a body portion via a body limb extremity. Manual application of the bandage can be assisted by pre-rolling the system into a "doughnut" shape or torus. The system, however, may conveniently be applied to the body portion by means of an applicator. The applicator can be a conventional expandible cylindrical shaped applicator of the type used for the application of tubular bandages.

The system for a hand or lower arm can be provided with a side hole inward of one end thereof prior to or after application to accommodate a thumb region of the hand.

After the system has been applied to the body portion, the hardenable resin can be hardened, for example by actinic (ultra-violet or visible light) radiation or by contact with water or moisture to form a cast about the body portion. The system, however, can be contacted with water or with moisture vapour prior to application thereof providing that the system is in its prehardened flexible and extensible state during application.

The bandage system of the invention may conveniently applied to the body portion by means of an applicator.

Thus in another aspect the present invention provides in combination an applicator and a cast bandage system of the invention, The applicator can be the conventional expandible cylindrical shaped applicator used for the application of tubular elastic bandages.

The composite tubular material of a hand or lower arm bandage system of the invention can conveniently be provided with a side hole towards one end thereof prior to or after application to accomodate a thumb region of a hand.

After the bandage system has been applied to the body portion, the hardenable resin on the outer fabric layer thereof can be hardened by for example ultra-violet light radiation or by contact with water or moisture to form a cast about the body portion.

The integrally formed padded splinting system complete with a hardenable resin which can be applied in a single operation offers many advantages over known bandages.

In United Kingdom Patent No. 1508695 and U.S. Pat. Nos. 3,307,537 and 3,656,475 there are disclosed bandage systems in which a tubular padding and the tubular fabric are applied to the body portion.

After application of the undercast padding/resin substrate the hardenable resin is applied to the substrate, for example from a spray can. These prior proposals suffer from a number of disadvantage. Firstly, like the conventional bandaging procedures, a number of separate steps are required. Care has to be taken to ensure that resin does not come into contact with non-bandaged parts of the body and, thirdly, it may be difficult to provde sufficient resin to immobilise the body portion with out deteriously effecting other properties such as breathablility. In connection with this latter point it may be difficult in getting sufficient resin into the substrate, particularly in those cases where the resin hardens in contact with air.

Thus in a further aspect the invention provides an orthopaedic cast formed from the orthopaedic cast bandage system of the invention.

Such an orthopaedic cast is preferably formed on the body portion by spraying water or moisture onto a water hardenable resin carried on the fabric of the outer layer of the composite tubular material of the bandage of the invention. Such a method of formation avoids the necessity of immersing the body portion and the cast bandage system applied thereto into water.

A water hardenable orthopaedic cast, however, can be formed by contacting the hardenable resin on the outer layer of the bandage system with water or moisture before it is applied to the body portion, for example by immersing the bandage system and optionally an applicator therefor in water. The bandage system can then be applied over the body portion before the resin sets in the usual manner. This method of forming the orthopaedic cast is highly suitable for the bandge system comprising an inner layer of padding material which has been rendered water impervious as hereinbefore described.

In yet a further aspect the present invention provides a method of preparing the cast orthopaedic bandage system of the invention which comprises forming a elastically extensible tubular composite material having an outer layer of fabric carrying a hardenable resin and an inner layer of padding material.

The outer layer of the composite tubular material can be formed by coating or impregnating a tubular fabric with a suitable hardenable resin, for example an polyurethane or acrylic propolymer, in a liquid state. The propolymer is preferably liquid at temperatures of 10° C. to 30° C. Solid or highly viscous propolymers however can be rendered liquid by any suitable method such as a hot melt or solvent method. The tubular fabric can be coated or impregnated with the liquid propolymer by any conventional method such as a two roller nip coating or impregnating method.

When the liquid prepolymer is a water hardenable resin it is desirable to dry the fabric for example by leaving it in vaccum, prior to coating or impregnation to reduce the water content thereof to not more than 1% by weight and preferably <0.1% weight.

When the inner padding layer of the composite tubular material comprises an elastically extensible lofted nonwoven fabric such a layer can be formed by attaching the tubular non-woven fabric to an elastic component.

The elastic component however preferably forms part of an elastic extensible tubular inner support fabric. In which case the inner layer can be formed by attaching the lofted non-woven fabric to an inner support layer of tubular elastically extensible fabric.

In such a process the lofted non-woven fabric layer can be provided with axial folds such as undulating folds to render the layer extensible prior to, during or after it attached to inner support layer of tubular elastically extensible fabric.

Prior to attachment the lofted non-woven fabric can be embossed or compressed to provide the undulating folded layer. The undulating folds in the layer can also be provided by bonding, for example by adhesive or heat bonding the layer in a folded form to discrete linear areas of the inner layer. In a preferred process the lofted non-woven fabric is attached to an expanded inner support layer of tubular elastic fabric and the composite layered tube allowed to contract. In such a process the composite tube are provided with undulating folds in axial direction thereof.

The tubular fabric can be expanded radially or widthwise in a substantially flat or collapsed form. The tubular fabric can conveniently be radially expanded over a mandrel of suitable size.

The tubular fabric can be expanded widthwise in a substantially flat state by means of a stenter for example a clip or pin stenter or passage around one or more stretching plates, for example one or a pair of such plates, preferably provided with tapered leading and trailing sides.

The tubular fabric can be an elastic fabric for example a woven or knitted fabric which comprises an elastic thread in its circumference. Alternatively the tubular fabric can be a tubular knitted fabric or a non woven fabric formed from a strip or sheet which has been rendered elastic by attaching tensioned elastic thread or threads in a circular or spiral fashion around the outside of the inner layer.

Preferably the outer surface of the innner support layer of tubular fabric containing or attached to the elastic component or components is provided with adhesive and the outer layer of lofted non-woven fabric strip or sheet is attached to inner layer by the adhesive. The adhesive can be provided prior of after expansion of the tubular fabric by any convenient coating method such as a solvent, hot melt or transfer coating method or by use of an adhesive coated strip component when forming the inner tubular fabric.

A preferred adhesive coating method for use in the process is a hot melt adhesive coating method using for example a spray or roller coating head. When such a method is employed during a process in which the tubular fabric is expanded widthwise in a flat form the hot melt adhesive will be coated on both outer surfaces of the flattened tubular fabric. The hot melt adhesive can advantageously be coated prior to expansion of the tubular fabric to inhibit penetration of the adhesive through the fabric such as stockinette fabric. In such a process the lofted non-woven fabric strip or sheet can be conveniently laminate to the adhesive coated surfaces of the expanded flat tubular fabric by passage through the nip of two pressure rollers. The rollers are preferaby adapted to be heated or cooled to facilitate the adhesive bonding. A second set of pressure rollers if necessary may be provided.

When the tubular fabric inner layer is expanded on a rotatable mandrel such as a driven rotatable mandrel, the adhesive, elastic or non-woven fabric components in thread or strip form can conveniently be applied around the inner layer while the mandrel is rotating. The tension in an elastic thread which is spirally wound around such a rotating mandrel can be adjusted by controlling the speed at which the elastic thread is fed into the mandrel.

In the process of the invention tubular padding material and the tubular fabric carrying the hardenable resin can be brought together to form the composite tubular material. In such a process the tubular padding material which forms the inner layer of the composite can conveniently be mounted on a mandrel or plate and the tubular fabric carrying the hardenable resin which forms the outer layer of the composite can be pulled over the inner layer to form the composite tubular material.

The expanded elastic composite layered tubed can then be removed from the mandrel or plate allowed to contract.

Individual cast bandage systems can be formed from suitable lengths of the elastic composite layered tube or cut from a continuous length of such tube.

Embodiments of the invention will be further described with reference to the accompanying drawings in which FIG. 1 a schematic sectioned perspective view of a casting system in accordance with the invention.

Figure 1:
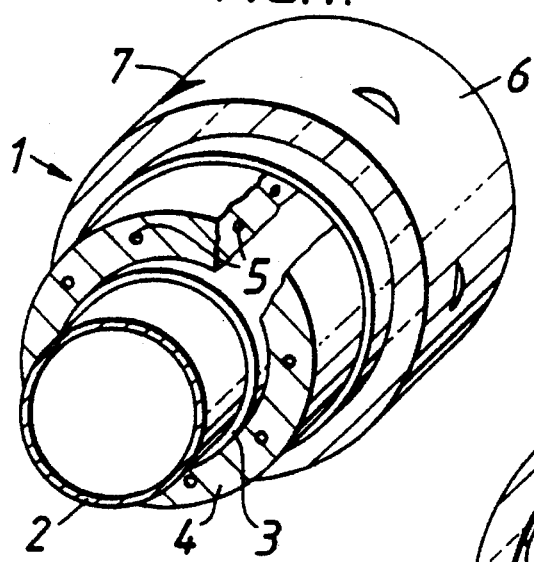

Referring to the drawings, a casting system (1) comprises an inner support layer (2) which may be of a knitted stockinette. Superimposed on the support layer 2 is a tubular layer (4) of a non-woven fabric such as SOFFBAN and adhered to the inner support layer by a layer of adhesive (3). Preferably the adhesive is present as a discontinuous layer.

Extending through the non-woven fabric layer are spirally wound elastic yarns 5.

An intermediate layer 6 of a resin impervious watersoluble material lies between the non-woven layer 4 and the outer layer 6.

The outer layer 6 is preferably a knitted substrate which carries a hardenable resin. Apertures 7 are provided in layer 6 to render the formed cast breathable.

Figure 2:
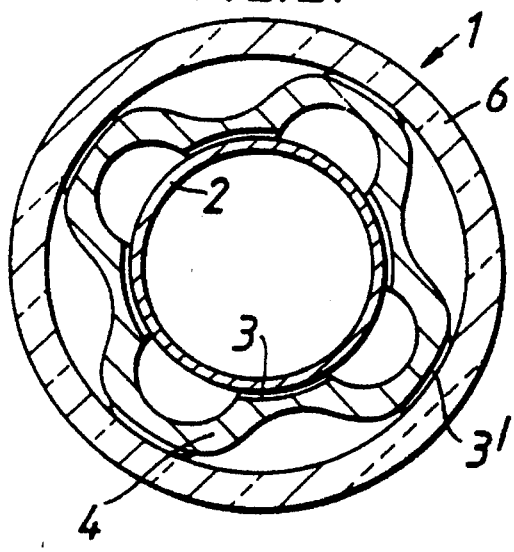
FIG. 2 is an end view or section of an embodiment of the invention.

FIG. 2 illustrates one embodiment in which the layer 4 is compressed into corrugations which extend circumferentially around the inner support tubular layer 2. The layer 4 is bonded to the inner support layer 2 and the outer layer 6 by suitable adhesive 3, $3^1$.

Figure 3:
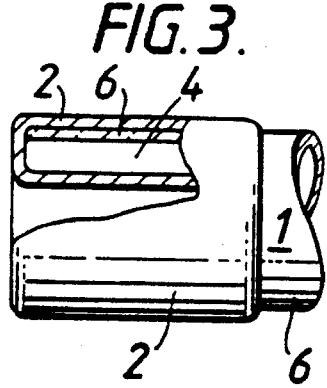
FIG. 3 is an schematic elevation of a casting composite in accordance with the invention and FIG. 4 is a general view of one form of casting system presented in the form of a torus.

In FIG. 3 the inner layer 2 extends beyond the end of the outer layer 6 and is wrapped around to form a cuff.

Figure 4:
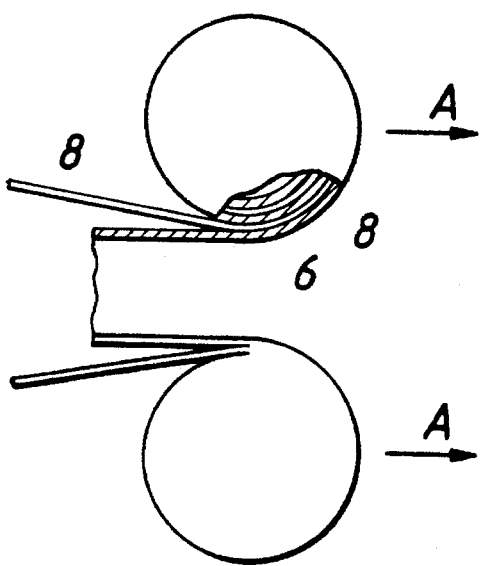

Referring to FIG. 4, the casting system 1 is rolled up to form a torus with an interliner sheet 8. The torus may be stretched over or applied over an undercast padding (not shown), for example, and unrolled in the direction shown by the arrows A, A.

The invention will be further illustrated by reference to the following examples.

EXAMPLE 1

Preparation of a Casting Bandage of the Invention

A knitted tube (length 30 cm, lay flat width 9.5 cm) in the form of sock minus its closed toe portion was impregnated with 300 ml of a liquid water hardenable polyurethane prepolymer resin by applying the resin to the tube and passing the tube between nip rollers to promote flow in resin into the fibres of the tube.

The tubular substrate was made of 70 % by weight of wool fibre yarns and 30 % by weight of polyamide fibre yarns loop-knitted into a terry pile lining. The tube had a weight of 33 g and a widthwise extension of 30 % and wall thickness of approximately 5 mm and a weight per unit area of 600 g/m².

Prior to impregnation the tube was predried in a vacuum oven at 60° C. for 24 hours and then packed in a water-proof foil pack.

The polyurethane prepolymer resin used was that used in Example 2 of British Patent Specification No. 2207141.

The tube was impregnated with approximately 300 g which is equivalent to a weight unit area of 5250 g/m² of the polyurethane prepolymer resin.

The widthwise extension of the bandage and the thickness of bandage material were similar to that respectively of the original tube material.

The casting system was then packaged in an aluminium foil pouch to inhibit premature hardening for example contact with moisture.

Preparation of an Orthopaedic Cast of the Invention

A tubular padding material (length 34 cm) similar to that disclosed in Example 3 of European Patent Application No 0356078 was applied to the wrist and lower arm of a volunteer. The casting bandage was removed from its pack, mounted on a conventional tubular bandage applicator and immersed in water to initiate hardening the bandage. The setting tubular bandage was then applied over the padding material and its end portions covered by folded overlap end portions of the padding material. A hole was made on side of applied bandage to accommodate the thumb region of the hand. The resin hardened in approximately 30 minutes to form an orthopaedic cast of the invention which was found to be sufficiently rigid to support and immobilise the wrist and lower arm of the volunteer.

EXAMPLE 2

The procedure of Example 1 was repeated except that the resin described in Example 1 of International Publication No. WO89/08405 was used.

The hardened cast was sufficiently rigid to support and immobilise the wrist and lower arm of the volunteer.

EXAMPLE 3

A tubular glass fibre substrate was knitted using a 50 Tex (6 µm filaments) yarn of E-Glass fibres (available from Pittsburgh Plate Glass Company).

The substrate was knitted to a 1×1 Rib Net Pattern using a 6-inch Cylinder and Dial Knitting Machine with 180 needles for each of the cylinder and dial.

A polyamide sheathed rubber yarn (Heathcote 'Fifties') was inlaid every 8th course of the knitted fabric.

The lay flat width of the knitted substrate was 7.3 cm and the wall thickness was about 3 mm.

A length of the tubular substrate was impregnated with the same polyurethane prepolymer employed in Example 1 to a weight of 600g/m². The resin impregnated substrate was then cut into a 30 cm length and sealed in an aluminium foil pouch.

Application of Cast

A length of elastic tubular stockinette (lay flat width 7.5 cm) was placed onto a tubular bandage applicator and applied to the forearm and around the crooked elbow elbow of a volunteer.

The resin impregnate substrate was removed from the pouch and rolled up to form a doughnut and immersed in a wate bath. The wet 'doughnut' was then stretched over the volunteer's hand and wrist and placed on the stockinette about 3 cm in from the distal end unrolled up the forearm and around the elbow. The end of the the resin impregnated substrate stopped about 3 cm short of the proximal end of the stockinette. The proximal and distal ends of the stockinette were then folded over the corresponding ends of the substrate to form cuffs.

The resin hardened after about 30 minutes sufficient to immobilise the arm in a comfortable position.

EXAMPLE 4

A cast bandage system of the invention was prepared by assembling a tubular padding material and a tubular fabric resin material on a applicator.

Preparation of the Tubular Padding Material

A tubular elastic stockinette (length 100 cm, lay-flat width 7.5 cm) was stretched over a flat plate former (length 125 cm width 25 cm) of general rectangular shape with curved ends.

The stockinette was a modified elasticated rib knitted tubular bandage (Tensogrip available from Smith & Nephew) containing cotton/viscose fibres and covered rubber threads spirally knitted into the fabric.

The outer surface of the stockinette was then sprayed with a thermoplastic polyurethane (Estane 5712 available from BF Goodrich) adhesive solution in methylene chloride and dried to give a weight per unit area of $13_{+}3g/m^2$. The coating was then covered with release paper and heated (temperature 125° C.) under pressure to firmly anchor the polyurethane adhesive to the stockinette. A strip (of sufficient size) of lofted non-woven fabric (SOFFBAN SYNTHETIC) was heat laminated under pressure to cover the adhesive coated surface of the stockinette on both sides of the former by feeding the stockinette (on the former) and the non-woven fabric through the nip of two pressure rollers whilst heating the side of the former opposite to that at which the non-woven fabric is laminated. The tubular padding material so formed was then cut into 30 cm lengths.

Preparation of the tubular fabric resin material

A length of elastic tubular stockinette (lay-flat width 10 cm) was impregnated with a polyurethane prepolymer a two roller nip impregnation method. The stockinette had knitted rib structure of polyester fibres and a spiral covered elastic thread. The stockinette was dried for 3 hours at 65° C. prior to being impregnated.

The polyurethane prepolymer resin used was prepared from the following components.

|  | % by weight |
| --- | --- |
| Isonate 143L | 47.86 |
| Isonate 240 | 14.69 |
| Voranol CP260 | 4.39 |
| PPG 1025 | 31.87 |
| Antifoam MSA | 0.15 |
| Methane Sulphonic acid (stabilizer) | 0.03 |
| KL-26 (catalyst) | 1.76 |

The CNO:OH ratio of the reactants was 7.74:2.00 Isonate 143L and Isonate 240 are modified Diphenylmethane diisocyanate available from Upjohn. voranol CP260 is a triol available from Dow Chemicals. PPG 1025 is a polypropylene glycol. Antifoam MSA is an antifoam available from Dow Chemicals. KL-26 is his (2,6-dimethyl morpholino-N-ethyl) ether.

In the preparation the isonate 143L in a suitable container is heated to 63° C., the Voranol CP-260 and PPG 1025 added in that order and the mixture allowed to react for 90 mins at a exothem raised temperature of 80° C. The reaction mixture was then cooled to 60°–63° C. and the isonate 240 added and allowed to react for 30 min. Antifoam MSA was then added and the reaction mixture cooled to 50° C. A vacuum was applied to the container and methane sulphonic acid and KL-26 added.

The polyurethane prepolymer resin had a viscosity of 20000 to 75000 centipoises at $25_{\pm}1°$ C. and a NCO content of >10%.

The stockinette was impregnated with weight unit area of 600 g/m$^2$ of the polyurethane prepolymer resin. The tubular fabric resin material was cut into 24 cm and 30 cm lengths.

Preparation of a cast bandage of the invention.

The tubular padding material (length 30 cm) was placed onto a conventional tubular bandage applicator and two lengths of tubular fabric resin material (length 24cm) placed over the padding material so that on the end portions (2–3 cm) were not covered. These end portions were then folded over the ends of the fabric resin material to form cuffs thereat. A further layer of tubular fabric resin material (length 30 cm) was applied over the composite to form the cast bandage system of the invention on an applicator. A thumb hole was then made in one side of the cast bandage system to render the system suitable for a wrist or lower arm cast or splint.

The cast bandage system was then applied over the hand to the wrist and lower arm of a volunteer by means of the applicator. The system was formed into a cast by spraying water onto outer fabric resin layer and moulding the wet bandage in place. The resin set in 30 mins to form a rigid but relatively comfortable cast.

We claim:

1. A casting system for application to a body portion, which comprises, before application of the casting system to said body portion, an outer layer tubular substrate carrying a water hardenable resin wherein the substrate is at least 2 mm thick and an inner layer comprising an undercast padding material comprising hydrophobic fibres or yarns.

2. A system as claimed in claim 1 wherein the substrate is a single layer.

3. A system as claimed in claim 1 wherein the substrate is a knitted substrate.

4. A system as claimed in claim 1 in which the resin carrying substrates is elastically extensible.

5. A system as claimed in claim 4 having an elasticity sufficient for it to recover to 60% of the width when stretched by 100% in the width direction.

6. A system as claimed in claim 4 in which the tubular material is rendered elastically extensible by means of an elastic yarn or thread.

7. A system as claimed in claim 1 wherein the tubular substrate comprises an elastic component.

8. A system as claimed in claim 1 wherein the tubular substrate comprises differently coloured materials.

9. A system as claimed in claim 8 wherein the substrate comprises more than one differently coloured yarns knitted into a pattern.

10. A system as claimed in claim 1 wherein the resin is a polyurethane prepolymer.

11. A system as claimed in claim 1 wherein resin is present in an amount of at least 50 gm per square meter of substrate.

12. A system as claimed in claim 1 wherein the resin carrying tubular substrate is provided with apertures.

13. A system as claimed in claim 12 wherein the substrate is a knitted substrate and the apertures are holes included within the knitting pattern.

14. A system as claimed in claim 12 wherein the apertures are from 1 to 100 mm$^2$ in area.

15. A system according to claim 1 wherein the inner layer is in the form of a tube.

16. A system as claimed in claim 1 in which the padding material comprises a lofted non-woven fabric.

17. A system as claimed in claim 16 in which lofted non-woven fabric has a thickness of 3 to 8 mm.

18. A system as claimed in claim 16 in which the lofted non-woven fabric is attached to an inner support layer of tubular elastic extensible material.

19. A bandage system as claimed in claim 18 in which the non-woven fabric and the inner support layer are bonded together.

20. A system as claimed in claim 1 in which walls of the inner layer of the tube comprises non-elastic material compressed into folds to form circumferential corrugations whereby the tube is adapted to be radially extensible.

21. A system as claimed in claims 20 wherein the inner support layer comprises a knitted fabric.

22. A system as claimed in claim 1 wherein the inner and outer layers are bonded together.

23. A system as claimed in claim 22 wherein the inner and outer layers are adhesively bonded together.

24. A system as claimed in claim 22 wherein the inner and outer layers are stitched together.

25. A system as claimed in claim 1 further comprising a resin-impermeable water-soluble layer intermediate the inner and outer layers.

26. A system as claimed in claim 1 within a sealed pouch.

27. A system as claimed in any one of claims 1 to 26 wherein the tubular substrate is rolled up into a torus.

28. A system as claimed in claim 26 within a water and moisture-proof pack.

29. In combination a bandage system of claim 1 and an applicator therefor.

30. An orthopaedic cast formed from the casting system claimed in claim 1.

* * * * *